US012788332B2

(12) United States Patent
Katyal et al.

(10) Patent No.: US 12,788,332 B2
(45) Date of Patent: Nov. 10, 2026

(54) COLOR CHANGING WEARABLE DEVICE BASED ON DIFFERENT BIOMARKERS OR WORKOUT ZONES

(71) Applicant: ULTRAHUMAN HEALTHCARE PVT LTD, Bengaluru (IN)

(72) Inventors: Piyush Katyal, Bangalore South (IN); Ankit Gupta, Bangalore South (IN)

(73) Assignee: ULTRAHUMAN HEALTHCARE PVT LTD, Bengaluru (IN)

( * ) Notice: Subject to any disclaimer, the term of this patent is extended or adjusted under 35 U.S.C. 154(b) by 0 days.

(21) Appl. No.: 19/335,149

(22) Filed: Sep. 22, 2025

(65) Prior Publication Data

US 2026/0013805 A1 Jan. 15, 2026

Related U.S. Application Data

(63) Continuation of application No. PCT/IN2025/050406, filed on Mar. 20, 2025.

(30) Foreign Application Priority Data

Mar. 22, 2024 (IN) ............................ 202441022394

(51) Int. Cl.
*A61B 5/00* (2006.01)
*A61B 5/0205* (2006.01)
*A61B 5/16* (2006.01)

(52) U.S. Cl.
CPC ............ *A61B 5/746* (2013.01); *A61B 5/0205* (2013.01); *A61B 5/165* (2013.01); *A61B 5/6802* (2013.01); *A61B 2562/166* (2013.01)

(58) Field of Classification Search
CPC ....... A61B 5/746; A61B 5/0205; A61B 5/165; A61B 5/6802; A61B 2562/166
See application file for complete search history.

(56) References Cited

U.S. PATENT DOCUMENTS

| | | | | |
|---|---|---|---|---|
| 7,602,303 | B2 * | 10/2009 | Douglas | G07C 9/28 340/539.11 |
| 10,700,774 | B2 * | 6/2020 | Panther | A61B 5/0002 |
| 2013/0072765 | A1 * | 3/2013 | Kahn | G16H 20/30 600/301 |
| 2016/0317067 | A1 * | 11/2016 | Lee | A61B 5/1123 |
| 2017/0102672 | A1 * | 4/2017 | Martin | G04B 25/04 |
| 2018/0103901 | A1 * | 4/2018 | Gandhi | G06F 3/015 |
| 2018/0307314 | A1 * | 10/2018 | Connor | G06F 3/017 |
| 2021/0235568 | A1 * | 7/2021 | Rattray | H04W 76/10 |
| 2021/0307664 | A1 * | 10/2021 | Bey | A61B 5/681 |
| 2022/0280105 | A1 * | 9/2022 | Dixit | A61B 5/02405 |

* cited by examiner

*Primary Examiner* — Daryl C Pope
(74) *Attorney, Agent, or Firm* — Renner, Otto, Boisselle & Sklar, LLP

(57) ABSTRACT

A wearable device to monitor health data of a user comprises an outer layer, an inner layer, and a middle layer positioned between the outer layer and the inner layer. The middle layer is a PCB housing a plurality of sensors configured to measure health data of the user. The PCB also houses a microcontroller for processing the health data measured by the plurality of sensors. A portion of the outer layer includes a color changing hardware. The microcontroller controls illumination of the color changing hardware when the health data satisfies a predefined condition.

8 Claims, 2 Drawing Sheets

COLOR CHANGING WEARABLE DEVICE BASED ON DIFFERENT BIOMARKERS OR WORKOUT ZONES

RELATED APPLICATIONS

This application is a continuation of International Application No. PCT/IN2025/050406, filed Mar. 20, 2025, which claims priority to Indian Application No. 202441022394, filed Mar. 22, 2024, each of which is hereby incorporated herein by reference in its entirety.

FIELD OF INVENTION

The present disclosure relates to smart wearable devices. More particularly, the present invention relates to a smart wearable device including a hardware for providing feedback on health data to a user.

BACKGROUND

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also correspond to implementations of the claimed technology.

Regular fitness monitoring is important for accomplishing long term wellness goals. Traditionally, fitness monitoring required manual recording of one's exercise activities. However, such manual recording is inconvenient and inaccurate.

Generally, the detection and monitoring of physiological parameters such as heart rate, blood pressure, oxygen saturation, and stress levels require stationary medical equipment, including ECG machines, blood pressure monitors, and pulse oximeters. These devices are often large, non-portable, and require a clinical setting or dedicated at-home monitoring systems, making them impractical for continuous, real-time tracking in a user's daily life.

For individuals who are constantly on the move, maintaining an awareness of their physiological and activity data in real time is challenging. The inability to continuously track body parameters can hinder proactive health management, limit early detection of potential health concerns, and reduce opportunities for timely lifestyle adjustments. Without access to immediate feedback, users may not recognize patterns in their biometrics that could indicate stress, fatigue, dehydration, or other health-related conditions, leading to potential long-term health risks.

While wearable devices such as smartwatches and fitness bands have emerged as solutions for tracking biomarkers and activity levels, these devices typically require users to access a companion application on a smartphone or other external device to view their real-time data. This dependency on secondary devices for feedback creates a delay in awareness, making it difficult for users to receive instant alerts or act upon physiological changes in the moment. The need to check a separate screen disrupts user engagement and reduces the effectiveness of real-time health monitoring.

Therefore, there is a need for a wearable device that not only continuously monitors user health data but also provides immediate, intuitive feedback directly on the wearable itself. The wearable device that visually communicates physiological and activity data through real-time color changes or patterns would enable users to track their biomarkers, and vitals in real-time to instantly interpret their health status without needing to check an external screen.

OBJECTS OF THE INVENTION

A general objective of the invention is to provide a smart wearable device capable of recording biomarkers of the user.

Another objective of the invention is to provide a smart wearable device capable of changing color based on the user biomarker data, and/or user selected fitness data such as step, calories, duration of workout, etc.

Yet another objective of the invention is to provide a smart wearable device capable of customization of the color and the mode setting based on the user preferences.

SUMMARY OF THE INVENTION

This summary is provided to introduce aspects related to a color changing wearable device based on different biomarkers or workout zones and the aspects are further described below in the detailed description. This summary is not intended to identify essential features of the claimed subject matter nor is it intended for use in determining or limiting the scope of the claimed subject matter.

In an embodiment, the present invention provides a wearable device, such as a smart ring to monitor health data of a user. The wearable device includes an outer layer, an inner layer, and a middle layer positioned between the outer layer and the inner layer. The middle layer is a PCB housing. The PCB housing includes a plurality of sensors configured to measure health data of the user and a microcontroller for processing the health data measured by the plurality of sensors. A portion of the outer layer includes a color changing hardware, and the microcontroller controls illumination of the color changing hardware when the health data satisfies a predefined condition.

In one aspect, the color-changing hardware includes at least one of light-emitting diodes (LEDs) and light-emitting polymers (LEPs).

In one aspect, the plurality of sensors includes SpO2 sensor, heartbeat sensor, photoplethysmogram (PPG) sensor, temperature sensor, motion sensor, electrocardiogram (ECG) sensor, barometer, accelerometer, and gyroscope.

In one aspect, a memory coupled to the microcontroller to store the health data.

In one aspect, the outer layer is made from a rigid, scratch-proof material including titanium, sapphire glass, hardened glass, fiber, and translucent material.

In one aspect, the inner layer is composed of a semi-transparent, translucent, or transparent material to allow an optical sensor to collect the user data when the wearable device is worn by the user.

In one aspect, the color-changing hardware is capable of illuminating in multiple colors and displaying various illumination patterns including blinking, revolving lights, dimming, and brightening at defined intervals.

In one aspect, a wireless module housed in the PCB, wherein the wireless module is configured to transmit the health data to a user device.

In one aspect, the health data includes biomarker data and user fitness data.

Other aspects and advantages of the invention will become apparent from the following description, taken in conjunction with the accompanying drawings, illustrating by way of example the principles of the invention.

BRIEF DESCRIPTION OF THE DRAWINGS

The accompanying drawings constitute a part of the description and are used to provide further understanding of the present disclosure. The drawings illustrate exemplary embodiments of the present disclosure and, together with the description, serve to explain the principles of the present disclosure.

DETAILED DESCRIPTION OF THE INVENTION

Figure 1:
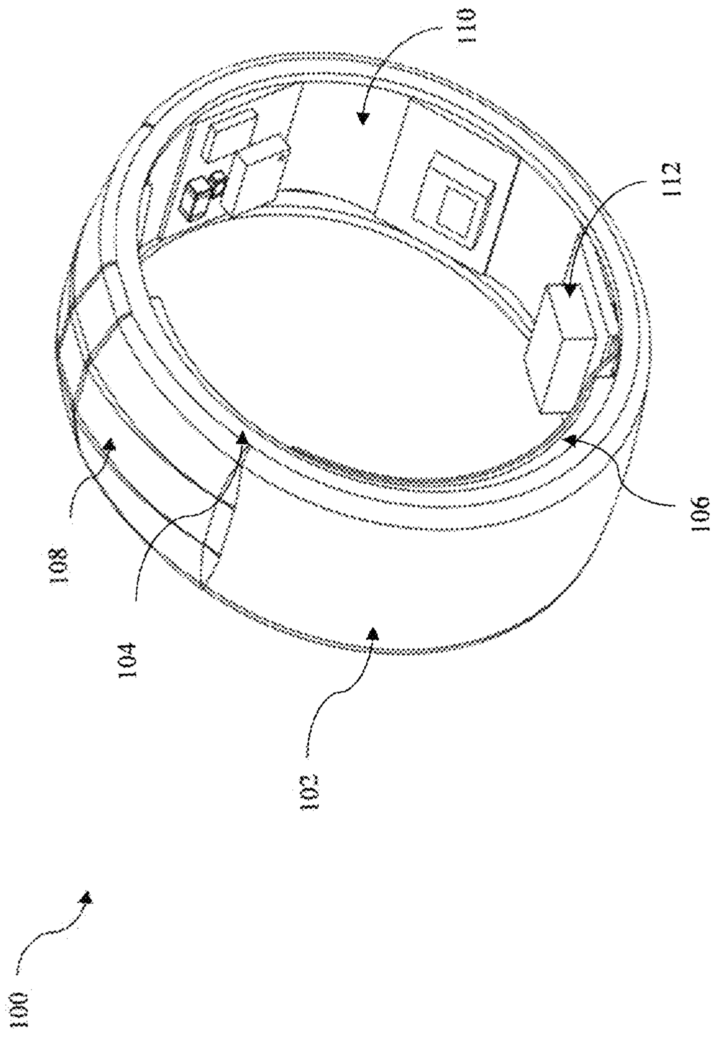
FIG. 1 illustrates a perspective view of a wearable device, in accordance with an embodiment of the present invention.

The description set forth below in connection with the appended drawings is intended as a description of various embodiments of the present disclosure and is not intended to represent the only embodiments in which the present disclosure may be practiced. Each embodiment described in this disclosure is provided merely as an example or illustration of the present disclosure, and should not necessarily be construed as preferred or advantageous over other embodiments. The description includes specific details for the purpose of providing a thorough understanding of the present disclosure. However, it will be apparent to those skilled in the art that the present disclosure may be practiced without these specific details.

Exemplary embodiments now will be described with reference to the accompanying drawings. The disclosure may, however, be embodied in many different forms and should not be construed as limited to the embodiments set forth herein; rather, these embodiments are provided so that this disclosure will be thorough and complete, and will fully convey its scope to those skilled in the art. The terminology used in the detailed description of the particular exemplary embodiments illustrated in the accompanying drawings is not intended to be limiting. In the drawings, like numbers refer to like elements.

It is to be noted, however, that the reference numerals used herein illustrate only typical embodiments of the present subject matter, and are therefore, not to be considered for limiting its scope, for the subject matter may admit to other equally effective embodiments.

The specification may refer to "an", "another", "one" or "some" embodiment(s) in several locations.

This does not necessarily imply that each such reference is to the same embodiment(s), or that the feature only applies to a single embodiment. Single features of different embodiments may also be combined to provide other embodiments.

As used herein, the singular forms "a", "an" and "the" are intended to include the plural forms as well, unless expressly stated otherwise. It will be further understood that the terms "includes", "comprises", "including" and/or "comprising" when used in this specification, specify the presence of stated features, integers, steps, operations, elements, and/or components, but do not preclude the presence or addition of one or more other features, integers, steps, operations, elements, components, and/or groups thereof. It will be understood that when an element is referred to as being "connected" or "coupled" to another element, it can be directly connected or coupled to the other element or intervening elements may be present. Furthermore, "connected" or "coupled" as used herein may include operatively connected or coupled. As used herein, the term "and/or" includes any and all combinations and arrangements of one or more of the associated listed items.

Unless otherwise defined, all terms (including technical and scientific terms) used herein have the same meaning as commonly understood by one of ordinary skills in the art to which this disclosure pertains. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The detailed description includes specific details for the purpose of providing a thorough understanding of the present disclosure. However, it will be apparent to those skilled in the art that the present disclosure may be practiced without these specific details.

Health parameters are usually monitored using stationary medical equipment like ECG and BP monitors, making it difficult for individuals to track their health parameters on the go. While wearable fitness devices exist, they often require users to check a smartphone app for real-time feedback, limiting immediate awareness and responsiveness. This lack of direct, instant feedback prevents users from making timely, informed decisions about their health and fitness. The smart ring addresses this challenge by integrating biometric sensors, real-time data processing, and color-changing illumination into a compact, wearable form and provides immediate, visual feedback on key health metrics customizable indicators.

FIG. 1 illustrates a perspective view of a wearable device, in accordance with an embodiment of the present invention. In an embodiment, the wearable device is compact in size, and designed to monitor health data of a user, including physiological biomarkers and fitness activity, while providing real-time, intuitive feedback through color-changing illumination. The wearable device visually communicates the health data and fitness status directly on the wearable device using a customizable color changing indicator.

The wearable device may be a smart ring (100), a smartwatch, a bracelet, or a necklace. The description has been provided successively with reference to the smart ring (100). The smart ring (100) may be made using a hypoallergenic material for allowing comfortable and continuous wear by the user. The smart ring (100) may comprise an outer layer (102), a middle layer (104), and an inner layer (106). The outer layer (102) may be made of a rigid and antirust material, such as titanium, transparent material, translucent material such as hardened glass, fibre, sapphire glass, or any other scratch proof hard material.

The outer layer (102) may include a plurality of housing to accommodate a color changing hardware (108). The housing is made by creating cavities in the outer layer (102) so that the color changing hardware (108) can be disposed in the housing. The color changing hardware (108) may be placed in the outer layer (102) in a variety of position such as facing outward or sideward of the smart ring (100). The color changing hardware (108) may include, but not limited to, light emitting diodes (LEDs), light emitting polymers (LEPs) etc. The color-changing hardware may be capable of illuminating in multiple colors and displaying various illumination patterns including blinking, revolving lights, dimming, and brightening at defined intervals that may be customized by the user of the smart ring (100).

Further, the middle layer (104) is positioned between the outer layer (102) and the inner layer (106). The middle layer (104) may include a printed circuit board housing (PCB). The PCB may be a flexible Printed Circuit Board (PCB) (110). The flexible PCB (or rigid Flex) (110) may house a plurality of sensors (206) (shown in FIG. 2) to capture biomarkers of the user.

Further, a microcontroller (112) may be mounted on the flexible PCB (110). The plurality of sensors (206) may be mounted on the flexible PCB (110). The microcontroller (112) may be connected to the flexible PCB (110). The plurality of sensors (206) may transmit values of the biomarkers detected by them to the microcontroller (112), in real-time. The microcontroller (112) may obtain values of the biomarkers from the plurality of sensors based on some internal and external triggers associated with the plurality of sensors. The microcontroller (112) may also store values of the biomarkers in a memory (210) (shown in FIG. 2). The memory (210) may be integral to the microcontroller (112) or connected externally on the flexible PCB (110).

Further, the microcontroller (112) may control the illumination of the color changing hardware (108) based on user preferences, and pre-defined conditions of biomarkers of the user. A wireless module (208) (shown in FIG. 2) may be mounted on the flexible PCB (110) to wirelessly communicate the biomarkers to a user device, such as a smartphone or a laptop. The wireless module (208) may work on one or more of Bluetooth and Near Field Communication (NFC).

In an embodiment, the wireless module (208) may include, but is not limited to, communication modules such as Wi-Fi, Bluetooth, Zigbee, LoRa, and cellular (4G/5G) modules, each designed for specific connectivity applications. For example, a Wi-Fi module, such as the ESP8266, may be a compact 18 mm×20 mm chip used in IoT devices to enable wireless data transmission over local networks. Similarly, a Bluetooth Low Energy (BLE) module, like the nRF52840, may be used in wearable devices for short-range communication with smartphones or other smart devices.

Further, the smart ring (100) may include a battery positioned anywhere between the outer layer (102), the middle layer (104), and the inner layer (106). In an embodiment, the battery may be a lithium-ion (Li-ion) battery, nickel-metal hydride (NiMH) battery, lead-acid battery, or solid-state battery, each designed for specific applications. For example, a lithium-ion battery, such as a 3.7V 3000 mAh rechargeable cell, may be used in smartphones, tablets, and wearable devices due to its high energy density and lightweight design. The battery may be used to power the plurality of sensors, the micro-controller, wireless module, and any other sensor used in the smart ring (100).

The inner layer (106) of the smart ring (100) may come in contact with the user's finger once the user wears the smart ring (100). The inner layer (106) may include a proximity sensor to detect the smart ring (100) is worn by the user or not. The inner layer (106) may be made of a semi-transparent, translucent, or completely transparent material. Materials such as glass, plastic, resin, or silicone may be used to fabricate the inner layer (106). Transparency of the inner layer (106) may allow the sensors to obtain reading from the finger of the user. For example, an optical sensor may be able to transmit light and obtain reflection of the light through the inner layer (106).

Figure 2:
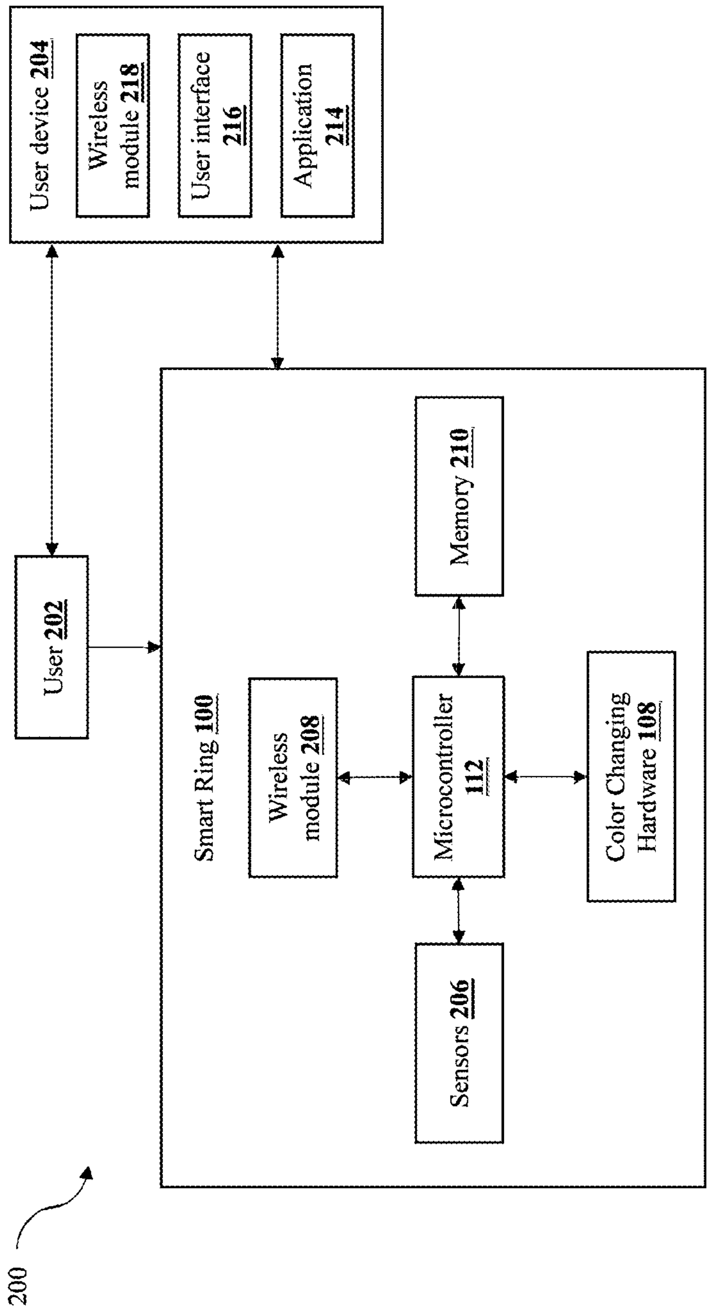
FIG. 2 illustrates a block diagram showing components of the wearable device and a user device connected with each other, in accordance with an embodiment of the present invention.

FIG. 2 illustrates a block diagram (200) showing components of the wearable device (100) and a user device (204) connected with each other, in accordance with an embodiment of the present invention. The smart ring (100) may communicate user instruction and user biomarker data to the user device (204). The connection between the smart ring (100) and the user device (204) is established by the wireless module (208).

Further, the smart ring (100) includes the plurality of sensors (206), the wireless module (208), the memory (210), and the color changing hardware (108). The plurality of sensors (206) includes $SpO_2$ sensor, heartbeat measurement sensor, photoplethysmogram (PPG) sensor, temperature sensor, motion sensor, ECG sensor, barometer, accelerometer, gyroscope etc. which may gather user's (202) biomarker data such as heartbeat, stress level, oxygen level, workout intensity, temperature etc. The plurality of sensors (206) provide real-time biomarker data to the smart ring (100) so as to analyse the user's biomarkers data as fast and efficiently as possible.

Further, the biomarker data of the user (202) may be stored in the memory (210). The memory (210) may be a Random-access memory (RAM) or a Read-only memory (ROM). Further, the memory (210) may store a set of computer readable instructions to perform various steps such as, illuminating a desired colour and pattern of the color changing hardware (108), transmitting user biomarkers data to the user device (204), etc.

Further, the smart ring (100) may transmit the user's biomarkers data gathered by the plurality of sensors (206) to the user device (204). The user device (204) may receive the biomarker data of the user (202) in real-time or a fixed time interval. The user device (204) may be, but not limited to, a smartphone, a tablet, a PC, or any other handheld device. Further, the user device (204) may include a wireless module (218), run an application (214), and provide a user interface (UI) (216). In one implementation, the user device (204) receives the user's biomarkers data from the smart ring (100) over a bluetooth connection implemented by the wireless module (208).

Upon receiving the biomarker data of the user (202), the application (214) of the user device (204) may determine a predefined condition or use-case based on the biomarker data. The application (214) may also render the biomarkers data to the user (202) via the UI (216) in real-time. The application (214) may be a software installed on the user device (204). The application (214) may store a plurality of predefined conditions based on the biomarker data of the user (202) such as, stress levels between 200 to 400, heartbeat rate above 100, oxygen level below 90, etc. The application (214) may also store details of colors and color patterns corresponding to each of the plurality of predefined conditions.

Upon determining a predefined condition based on the biomarker data, the application (214) may transmit the color and a colour pattern corresponding to the determined pre-defined condition to the smart ring (100) in order to illuminate the color changing hardware (108) in the received color and colour pattern. The color changing hardware (108) may illuminate in a plurality of colours such as, red, blue, green, yellow, pink etc. based on the pre-defined conditions of the biomarker data or the workout zones, and a plurality of color patterns such as, various level of glow, various patterns such as blinking, revolving lights, dimming and brightening of color changing hardware (108) in a defined interval of time, changing colour in defined patterns, etc.

In an embodiment, the user (202) may customize the illumination of the color changing hardware (108) based on the customized pre-defined conditions. The user (202) may access the application (214) to customize the pre-defined conditions and the corresponding color and colour pattern. The user (202) may customize based on the various parameters such as, changing color based on stress level, altering color when the heart rate falls outside a user-selected range, modifying color in response to the current step count or upon achieving a step goal, displaying different colours for various workout zones, changing color when temperature falls outside a selected range. Further, the smart ring (100) manages the data sharing and the Logic for changing of color and color pattern of the color changing hardware (108).

In one exemplary situation, during usage, a user may wear a smart ring on his finger and the smart ring monitors a plurality of biomarkers such as heartbeat, oxygen level and stress levels, and/or user selected fitness data such as step, calories, duration of workout, etc of the user using the sensors embedded in the smart ring. For example, the smart ring determines the heartbeat of the user as 80, oxygen level as 95, and stress level as 300. The smart ring transmits the biomarker data to a user device (smartphone of the user) to analyse and determine a pre-defined condition based on the latest biomarker data of the user.

Further, each pre-defined condition corresponds to a color or color pattern of the color changing hardware. The pre-defined condition and the corresponding color or color pattern of the smart ring are, stress level between 200 to 400 corresponds to a red color and rapid blinking of the color changing hardware, heartbeat between 100 to 120 corresponds to a blue color and revolving illumination of the color changing hardware, and oxygen level between 80 to 90 corresponds to green color and blinking pattern in an interval of 2 seconds of the color changing hardware. Further, the user device compares the biomarker data with the pre-defined conditions to check if any biomarker data falls in any of the pre-defined condition. The user device determines the predefined condition with stress level range 200 to 400 as the stress level of the user is 300.

In another exemplary situation, the smart ring determines the heartbeat of the user as 110, oxygen level as 99, and stress level as 700 during a workout. The smart ring may illuminate the color changing hardware based on a combined pre-defined condition such as, a high intensity workout corresponding to a high heartbeat, high oxygen level and high stress and corresponds to a bright red illumination with random blinking pattern, or a low intensity workout corresponding to a above average heartbeat, high oxygen level and mild stress and corresponds to a green illumination with 2 second interval blinking, etc. The smart ring then illuminates the color changing hardware (108) based on combined three conditions, in this case the smart ring illuminates in bright red color with random blinking.

Further, the user device may transmit the determined pre-defined condition and the corresponding color and color pattern to the smart ring. The smart ring then illuminates the color changing hardware using a microcontroller based on the pre-defined condition. The color changing hardware of the smart ring illuminates in red color and blinks rapidly to indicate the user that stress levels are between 200 to 400.

In an embodiment, the pre-defined conditions of the biomarker data may be customized by the user using the application of the user device. The user may customize the pre-defined conditions by adding, removing or modifying the existing conditions. Further, the user may customize the colour pattern corresponding to each of the pre-defined condition of the user biomarker via the UI of the user device.

Technical Advancement

One of the many technical advantages of the proposed invention is to provide personalised, intuitive feedback directly on the ring, eliminating the need for additional devices to monitor health and fitness metrics. The proposed invention offers seamless integration with a user's lifestyle through its wireless connectivity to smartphones for customizable settings. The proposed invention offers a dedicated application installed on a user device to customize the settings of the ring remotely, effectively controlling the lighting function based on the user preference. The application also offers a real-time view of the biomarkers of the user on the user device.

Aspects of the present disclosure may be implemented as computer program products that comprise articles of manufacture. Such computer program products may include one or more software components which are implementable by a processor or group of processors and said software components may include, for example, applications, software objects, methods, data structure, and/or the like. In some embodiments, a software component may be stored on one or more non-transitory computer-readable media, which computer program product may comprise the computer-readable media with software component, comprising computer executable instructions, included thereon.

The figures of the disclosure are provided to illustrate some examples of the disclosure described. The figures are not to limit the scope of the depicted embodiments or the appended claims. Aspects of the disclosure are described herein with reference to the disclosure to example embodiments for illustration. It should be understood that specific details, relationships, and method are set forth to provide a full understanding of the example embodiments. One of ordinary skill in the art recognize the example embodiments can be practiced without one or more specific details and/or with other methods.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

It is to be understood that the disclosure is not to be limited to the specific embodiments disclosed, and that modifications and other embodiments are intended to be included within the scope of the appended claims. Although specific terms are employed herein, they are used in a generic and descriptive sense only and not for purposes of limitation, unless described otherwise.

We claim:

1. A wearable device to monitor health data of a user, comprising:

an outer layer, an inner layer, and a middle layer positioned between the outer layer and the inner layer, wherein the middle layer is a PCB configured to house, between the outer layer and the inner layer:

a plurality of sensors configured to measure health data of the user; and a microcontroller for processing the health data measured by the plurality of sensors, wherein the outer layer includes a housing defining one or more cavities configured to accommodate a color changing hardware such that the color changing hardware is disposed in the one or more cavities on a side of the middle layer opposite the inner layer, and the microcontroller controls illumination of the color changing hardware when the health data satisfies a predefined condition, wherein the wearable device is a smart ring, wherein the inner layer is configured to contact a finger of the user when the smart ring is worn by the user, and wherein the inner layer is composed of a semi-transparent, translucent, or transparent material to allow an optical sensor to collect the user data from the finger of the user through the inner layer when the wearable device is worn by the user.

2. The wearable device of claim 1, wherein the color-changing hardware includes at least one of light-emitting diodes (LEDs) and light-emitting polymers (LEPs).

3. The wearable device of claim 1, wherein the plurality of sensors includes SpO2 sensor, heartbeat sensor, photoplethysmogram (PPG) sensor, temperature sensor, motion sensor, electrocardiogram (ECG) sensor, barometer, accelerometer, and gyroscope.

4. The wearable device of claim 1, further comprises a memory coupled to the microcontroller to store the health data.

5. The wearable device of claim 1, wherein the outer layer is made from a rigid, scratch-proof material including titanium, sapphire glass, hardened glass, fiber, and translucent material.

6. The wearable device of claim 1, wherein the color-changing hardware is capable of illuminating in multiple colors and displaying various illumination patterns including blinking, revolving lights, dimming, and brightening at defined intervals.

7. The wearable device of claim 1 further comprises a wireless module housed in the PCB, wherein the wireless module is configured to transmit the health data to a user device.

8. The wearable device of claim 1, wherein the health data includes biomarker data and user fitness data.

* * * * *